United States Patent [19]

Graves

[11] Patent Number: 5,510,493

[45] Date of Patent: Apr. 23, 1996

[54] PROCESS FOR ALKYLATION WITH TRIAZOLES

[75] Inventor: Deborah D. Graves, Blue Bell, Pa.

[73] Assignee: Rohm and Haas Company, Philadelphia, Pa.

[21] Appl. No.: 337,710

[22] Filed: Nov. 14, 1994

[51] Int. Cl.[6] .................... C07D 249/14; C07D 249/08
[52] U.S. Cl. ..................... 548/267.4; 548/262.2; 548/265.2; 548/266.8; 548/267.8; 548/268.6
[58] Field of Search ............ 548/262.21, 266.8, 548/267.4, 267.8, 268.6, 265.2

[56] References Cited

U.S. PATENT DOCUMENTS

| | | | |
|---|---|---|---|
| 4,366,165 | 12/1982 | Miller et al. | 424/269 |
| 4,920,139 | 4/1990 | Fujimoto | 514/383 |
| 5,087,635 | 2/1992 | Shaber | 514/383 |

OTHER PUBLICATIONS

Baker et al., Synthesis and Chemistry of Agrochemicals, American Chemical Society, pp. 318–327 (1987).

*Primary Examiner*—Patricia L. Morris
*Attorney, Agent, or Firm*—Joseph F. Leightner

[57] ABSTRACT

The present invention provides an improved process for the production of triazoles of the formula:

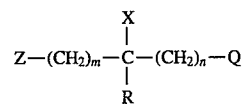

wherein Z is an optionally substituted $(C_6-C_{10})$aryl group;

R is a hydrogen atom, a $(C_1-C_{12})$alkyl group, a $(C_3-C_8)$ cycloalkyl group, a $(C_2-C_8)$alkenyl group, a $(C_5-C_8)$ cycloalkenyl group, a $(C_2$ to $C_8)$alkenyl group, an optionally substituted $(C_7$ to $C_{14})$aralkyl group, a $(C_2$ to $C_4)$alkynoxy group, an optionally substituted $(C_6$ to $C_{10})$aryloxy group or a hydroxy group;

Q is an optionally substituted 1-(1,2,4-triazolyl) or 4-(1,2,4-triazolyl);

X is hydrogen or CN;

m is zero or one;

n is one or two the triazoles are provided in higher yields than previously obtained. The improved yields are obtained by the incremental or continuous addition of triazole salts to compounds having the formula:

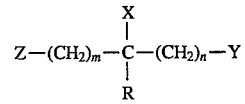

and m, n, R, X, Y, and Z are the same as defined above.

19 Claims, No Drawings

PROCESS FOR ALKYLATION WITH TRIAZOLES

The present invention relates to an improved process for alkylation with triazoles, in particular the present invention is directed to an improved process for the preparation of optionally substituted 1H-(1,2,4-triazole).

Triazole compounds and the fungicidal properties of these compounds are known in the art. U.S. Pat. No. 4,366,165 discloses biologically active 1 and 4 aryl cyanoalkyl-1,2,4 triazoles. U.S. Pat. No. 5,087,635 discloses alpha-aryl-alpha-phenethyl- 1H-1,2,4-triazole-1-propanenitriles as effective broad-spectrum systemic fungicides effective in controlling phytopathogenic fungi.

Inasmuch as the biological activity of triazoles is known, improved processes for providing these compounds are desired to reduce the manufacturing cost of these compounds.

In particular the present invention relates to a process for the preparation of compounds of the formula:

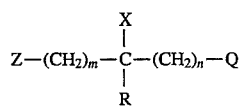

wherein Z is an optionally substituted $(C_6-C_{10})$aryl group; R is a hydrogen atom, a $(C_1-C_{12})$alkyl group, a $(C_3-C_8)$cycloalkyl group, a $(C_2C_8)$alkenyl group, a $(C_5-C_8)$cycloalkenyl group, a $(C_2$ to $C_8)$alkenyl group, an optionally substituted $(C_7$ to $C_{14})$aralkyl group, a $(C_2$ to $C_4)$alkynoxy group, an optionally substituted $(C_6$ to $C_{10})$aryloxy group or a hydroxy group; Q is an optionally substituted 1-(1,2,4-triazolyl) or 4-(1,2,4-triazolyl); X is hydrogen or CN;

m is or is an integer with a value zero or one; n is an integer one or two;

which comprises reacting a compound of the formula:

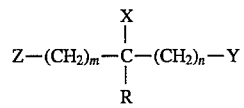

wherein Z, R, X, m and n are as defined above and Y is selected from the group consisting of halo, tosyl and mesyl with a triazole salt of the formula:

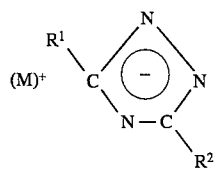

wherein M is any cation or mixture of cations; $R^1$ and $R^2$ may be the same or different and have the same definition as R hereinabove and the triazole salt is added to the intermediate compound in multiple additions. The multiple additions may contain the same or variable amounts of the triazole salt. Preferably the same amount of triazole salt is added in each of the incremental additions. The reactions are carried out in a temperature range of from about 50° C. to about 190° C. and preferably in a range from about 120° C. to about 160° C.

In a more preferred embodiment R is$(C_1-C_8)$alkyl, $(C_3-C_6)$cycloalkyl, or $(C_3-C_6)$alkenyl; $R^1$ and $R^2$ are hydrogen and M is a cation selected from Group IA of the Periodic Table, especially sodium or potassium.

In another embodiment of the present invention, the triazole salt addition is made in a continuous addition. Continuous addition is defined to be the addition of triazole salt over more than 20% of the reaction period. More preferably the triazole salt is added over 50% and in a most prefered embodiment over 60% of the reaction period. The rate at which the triazole salt is added may be constant or varied during the reaction. In a preferred embodiment, the triazole salt is added to the reactor in a continuous manner at a uniform rate.

The triazole salt may be added as a solid or in a solution or slurry in a suitable solvent. Preferably the triazole salt is added with no diluent. For ease of separation, a minimum amount of a suitable solvent should be used, such as for example dimethyl sulfoxide (DMSO). Slurries employing suitable solvents such as xylene, toluene and dimethyl foramide may be used to add the triazole salt to the reactor.

It has been surprisingly discovered that the addition rate of the triazole salt is an important variable in the percent yield obtained in the claimed process. The present invention improves the yield of triazole product by about 2%, preferably by more than 4% and in most prefered method by greater than 6% when compared to reactions in which the triazole salt is added to the reactor at one time. By the methods of the present invention, yields of greater than 94%, preferably greater than 96%, and most preferably greater than 97% are achieved based upon the amount of intermediate compound employed. Without wishing to be bound by any theory it is believed that the improved yields provided by the method of the present invention are due to the higher selectivity for the formation of 1H-(1,2,4-triazole). The 1H-(1,2,4-triazole) is selectively produced by the presently claimed method over the 4H-(1,2,4-triazole) in a ratio of about 15:1 versus 13:1 for the single addition method disclosed in the earlier discussed patents. Previously there was no recognition or suggestion in the art that the manner in which the triazole salt is added would have any effect the selectivity of the product produced or on product yields.

The term "aryl," as used in defining the substituents Z and R in the present specification and claims, is meant an aromatic ring structure of from 6 to 10 carbon atoms, preferably a phenyl or naphthyl group which is optionally substituted with up to three substituents, preferably with up to two substituents selected from the group consisting of halogen, nitro, trihalomethyl, cyano, $(C_1$ to $C_4)$alkyl, $(C_1$ to $C_4)$alkoxy, $(C_1$ to $C_4)$alkylthio, $(C_1$ to $C_4)$alkylsulfinyl and $(C_1$ to $C_4)$alkylsulfonyl.

Typical aryl substituents encompassed in this invention are phenyl, naphthyl, 4-chlorophenyl, 2,4-dibromophenyl, 3,5-difluorophenyl, 2,4,6-trichlorophenyl, 2,3,5-tribromophenyl, 3,4-dichlorophenyl, 2-chloro-4-iodophenyl, 3-chloro-4-nitrophenyl, 2,4-dinitrophenyl, 3,4,5-trimethylphenyl, 2-nitro-4-methoxyphenyl, 2-chloronaphthyl, 2-nitronaphthyl, 2,4-dimethoxyphenyl, 4-trifluoromethylphenyl, 2-nitro-4-trifluoromethylphenyl, 3,5-dimethylthiophenyl, 2-cyano-5-methylphenyl, 2,4-dimethylsulfinylphenyl, 2,4-dimethylsulfonylphenyl, 2,4-diiodonaphthyl, 2-iodo-4-methylphenyl and the like.

The term "aralkyl" is used, in defining the substituent R in the present specification and claims, to define an aralkyl group wherein the alkyl chain is from 1 to 4 carbon atoms and can be branched or straight chained and the aryl portion of the group is meant to be defined as above. Typical aralkyl substituents encompassed in this invention are 2,4-dichlorobenzyl, 2,4-dibromobenzyl, 2,5-dinitrobenzyl, 2,4,6-trichlorobenzyl, 3,5-dimethoxyphenethyl, 2,5-di(methylthio)phenylpropyl, 2,4-diiodophenyl- 2-methyl-propyl, 3,4- di(methylsulfiny)lbenzyl, 2,3-di(methylsulfonyl)phenylethyl, 2,4,5-trimethylphenylbutyl, 2,4-dicyanonaphthylmethyl, 2-nitronaphthylethyl, 2-nitronaphthylpropyl, 2,4-dibromonaphthylbutyl and the like.

The term "alkyl," as utilized in defining the substituent R in the present specification and claims, is meant to include both branched and straight chained alkyl groups of from 1 to 12 carbon atoms. Typical alkyl groups which are encompassed by the use of this term in defining this invention are methyl, ethyl, propyl, isopropyl, n-butyl, sec-butyl, isobutyl, tert-butyl, pentyl, neopentyl, iso-pentyl, hexyl, heptyl, iso-octyl, nonyl, decyl, iso-decyl, undecyl, dodecyl and the like.

In the definition of Q the term "optionally substituted 1H-(1,2,4-triazolyl) is meant to include unsusubstituted 1H-(1, 2,4-triazolyl) and substituted which can be substituted with up to two substitutes selected from the group consisting of halogen, ($C_1$ to $C_4$)alkyl, nitro and cyano.

EXAMPLE 1

Preparation of Fenbuconazole (Comparative Example)

To a 4 necked, 300 ml flask equipped with an overhead stirrer, reflux condenser thermometer and heating mantle, 58.0 grams (0.191 moles) of 1-chloro-2-cyano-2-phenyl-4-(4-chlorophenyl)butane, 159.71 grams of DMSO (2.04 moles) were charged to the flask and heated to 150° C. Sodium triazole (23.10 grams 0.25 moles) was added to the flask and the reaction was allowed to continue at 150° C. until the reaction was completed (approximately 5.5 to 6 hours). DMSC) was removed from the flask via vacuum distillation performed by ramping the temperature from 80° to 140° C. The distillation was ended and the flask vented and cooled. The product was washed by adding water (120 grams) and methylene chloride (100 grams) to the flask.

The contents of the flask were transferred into a seperatory funnel. The organic product was transferred into an Erlymeyer flask and the aqueous layer was discarded. The organic product was washed with 30 grams of saturated NaCl in 30 grams of water. Weight percent gas chromatography compared to standard determined that a total of 71.04 grams of crude product, containing 59.2 grams (0.176 moles) of the active ingredient, fenbuconazole was recovered for a yield of 92%.

EXAMPLE 2

Incremental Addition of Sodium Triazole to Provide Fenbuconazole

The equipment and raw materials of Example 1 were used to investigate the incremental addition of the triazole and its effect on the yield of fenbuconazole.

The identical levels of Intermediate I and DMSO were charged to the flask and heated to 150° C. Sodium triazole (3.85 grams/0.04 moles) was initially added to the flask to initiate the reaction. One hour later 4 grams/0.044 moles of sodium triazole was added to the flask. Four subsequent additions (4 grams/0.044 moles) of sodium triazole were made at one hour time intervals. The reaction was allowed to run until completion.

The product was then isolated and purified using the procedure outlinedin Example 1. A total of 68.78 grams of crude product containing 60.1 grams of fenbuconazole was isolated for a yield of 94%.

EXAMPLE 3

Incremental Addition of Sodium Triazole to Provide Myclobutanil

Using similar equipment and techniques as described in Example 2 above, multiple additions of sodium triazole are reacted with α-chloromethyl-α-(4-chlorophenyl)hexane nitrile to provide higher yields of α-butyl-α-(4-4-chlorophenyl)- 1H-1,2,4,-triazole-1-propanenitrile (myclobutanil).

I claim:
1. A process for the preparation of a triazole compound of the formula:

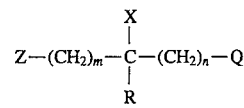

wherein Z is an unsusubstituted ($C_6$–$C_{10}$)aryl group or a substituted ($C_6$–$C_{10}$)aryl group with up to three substituents selected from the group consisting of halogen, nitro, trihalomethyl, cyano, ($C_1$–$C_4$)alkyl, ($C_1$–$C_4$)alkoxy, ($C_1$–$C_4$)alklthio, ($C_1$–$C_4$)alkylsulfinyl and ($C_1$–$C_4$)alkylsulfonyl;

R is a hydrogen atom, a ($C_1$–$C_{12}$)alkyl group, a ($C_3$–$C_8$)cycloalkyl group, a ($C_2$–$C_8$)alkenyl group, a ($C_5$–$C_8$)cycloalkenyl group, a ($C_2$ to $C_8$)alkenyl group, an unsubstituted ($C_7$ to $C_{14}$)aralkyl group or a ($C_7$ to $C_{14}$)aralkyl group substituted with up to three substituents selected from the group consisting of halogen, nitro, trihalomethyl, cyano, ($C_1$–$C_4$)alkyl, ($C_1$–$C_4$)alkoxy, ($C_1$–$C_4$)alklthio, ($C_1$–$C_4$)alkylsulfinyl and ($C_1$–$C_4$)alkylsulfonyl; a ($C_2$ to $C_4$)alkynoxy group, an unsubstituted ($C_6$ to $C_{10}$)aryloxy group or ($C_6$ to $C_{10}$)aryloxy group substituted with up to three substituents selected from the group consisting of halogen, nitro, trihalomethyl, cyano, ($C_1$–$C_4$)alkyl, ($C_1$–$C_4$)alkoxy, ($C_1$–$C_4$)alklthio, ($C_1$–$C_4$)alkylsulfinyl and ($C_1$–$C_4$)alkylsulfonyl; or a hydroxy group; Q is an unsubstituted 1-( 1,2,4-triazolyl) or 4-(1,2,4-triazolyl) or substituted 1-(1,2,4-triazolyl) or 4-( 1,2,4-triazolyl) with two substituents selected from the group consisting of halogen, C1–C 4)alkyl, nitro and cyano; X is hydrogen or CN;

m is in an integer with a value of zero or one; n is an integer with a value of one or two which comprises the reaction of an intermediate compound of the formula:

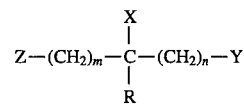

wherein Z, R, X, m and n are as defined above and Y is selected front halo, tosyl and mesyl with a triazole salt of the formula:

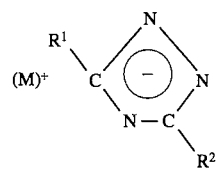

wherein M is a cation or a mixture of cations; $R^1$ and $R^2$ are the same or different and have the same definition as R; and the triazole salt is added to the intermediate compound in multiple additions;

such that the ratio of the production of the 1H-(1,2,4-triazole) to the 4H-(1,2,4-triazole) is greater than about 13:1.

2. The process of claim 1 wherein the triazole salt is added continuously.

3. The process of claim 1 wherein the triazole salt is sodium triazole and the intermediate compound is 2-chloromethyl-2-(4-chlorophenyl)hexane nitrile.

4. The process of claim 1 wherein the resulting triazole product is α-butyl-α-(4-chlorophenyl(1H-1,2,4-triazole-1-propanenitrile.

5. The process of claim 1 wherein the triazole salt is sodium triazole and the intermediate compound is 1-chloro-2-cyano-2-phenyl-4-(4-chlorophenyl)butane.

6. The process of claim 1 wherein the resulting triazole product is α-[2-(4-chlorophenyl)]ethyl-α-phenyl-(1H-1,2,4-triazole)-1-propaneenitrile.

7. The process of claim one in which the ratio of the production of the 1H-( 1,2,4-triazole) to the 4H-(1,2,4-triazole) is greater than about 15:1

8. A process for the preparation of a triazole compound of the formula:

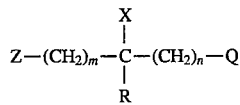

wherein Z is an unsusubstituted (C$_6$–C$_{10}$)aryl group or a substituted (C$_6$– C$_{10}$)aryl group with up to three substituents selected front the group consisting of halogen, nitro, trihalomethyl, cyano, (C$_1$–C$_4$)alkyl, (C$_1$–C$_4$)alkoxy, (C$_1$–C$_4$)alklthio, (C$_1$–C$_4$)alkylsulfinyl and (C$_1$–C$_4$)alkylsulfonyl;

R is a hydrogen atom, a (C$_1$–C$_{12}$)alkyl group, a (C$_3$–C$_8$)cycloalkyl group, a (C$_2$–C$_8$)alkenyl group, a (C$_5$–C$_8$)cycloalkenyl group, a (C$_2$ to C$_8$)alkenyl group, an unsubstituted (C$_7$ to C$_{14}$)aralkyl group or a (C$_7$ to C$_{14}$)aralkyl group substituted with up to three substituents selected front the group consisting of halogen, nitro, trihalomethyl, cyano, (C$_1$–C$_4$)alkyl, (C$_1$–C$_4$)alkoxy, (C$_1$–C$_4$)alklthio, (C$_1$–C$_4$ )alkylsulfinyl and (C$_1$–C$_4$)alkylsulfonyl; a (C$_2$ to C$_4$)alkynoxy group, an unsubstituted (C$_6$ to C$_{10}$)aryloxy group or (C$_6$ to C$_{10}$)aryloxy group substituted with up to three substituents selected from the group consisting of halogen, nitro, trihalomethyl, cyano, (C$_1$–C$_4$)alkyl, (C$_1$–C$_4$)alkoxy, (C$_1$–C$_4$)alklthio, (C$_1$–C$_4$)alkylsulfinyl and (C$_1$–C$_4$)alkylsulfonyl or a hydroxy group; Q is an unsubstituted 1-(1,2,4-triazolyl) or 4-( 1,2,4-triazolyl) or substituted 1-(1,2,4-triazolyl) or 4-(1,2,4-triazolyl) with two substituents selected front the group consisting of halogen, (C$_1$–C$_4$)alkyl, nitro and cyano; X is hydrogen or CN;

m is in an integer with a value of zero or one; n is an integer with a value of one or two which comprises the reaction of an intermediate compound of the formula:

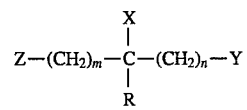

wherein Z, R, X, m and n are as defined above and Y is selected from halo, tosyl and mesyl with a triazole salt of the formula:

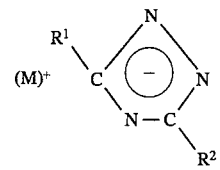

wherein M is a cation or a mixture of cations; R$^1$ and R$^2$ are the same or different and have the same definition as R; and the triazole salt is added to the intermediate compound in multiple additions;

such that the yield of the triazole compound is improved by greater than about 2% by weight over the reactions in which the triazole salt is added to the reactor at one time.

9. The process of claim 8 wherein the triazole salt is added continuously.

10. The process of claim 8 wherein the triazole salt is sodium triazole and the intermediate compound is 2-chloromethyl-2-(4-chlorophenyl)hexane nitrile.

11. The process of claim 8 wherein the resulting triazole product is α -butyl-α-(4-chlorophenyl)-(1H-1,2,4-triazole)-1-propanenitrile.

12. The process of claim 8 wherein the triazole salt is sodium triazole and the intermediate compound is 1-chloro-2-cyano-2-phenyl-4-(4-chlorophenyl)butane.

13. The process of claim 8 wherein the resulting triazole product is α-[2-(4 -chlorophenyl)ethyl-α-phenyl-(1H-1,2,4-triazole)-1-propanenitrile.

14. A process for the preparation of a triazole compound of the formula:

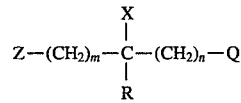

wherein Z is an unsusubstituted (C$_6$–C$_{10}$)aryl group or a substituted (C$_6$–C$_{10}$)aryl group with up to three substituents selected from the group consisting of halogen, nitro, trihalomethyl, cyano, (C$_1$–C$_4$)alkyl, (C$_1$–C$_4$)alkoxy, (C$_1$–C$_4$)alklthio, (C$_1$–C$_4$)alkylsulfinyl and (C$_1$–C$_4$)alkylsulfonyl;

R is a hydrogen atom, a (C$_1$–C$_{12}$)alkyl group, a (C$_3$–C$_8$)cycloalkyl group, a (C$_2$–C$_8$)alkenyl group, a (C$_5$–C$_8$)cycloalkenyl group, a (C$_2$ to C$_8$)alkenyl group, an unsubstituted (C$_7$ to C$_{14}$)aralkyl group or a (C$_7$ to C$_{14}$)aralkyl group substituted with up to three substituents selected from the group consisting of halogen, nitro, trihalomethyl, cyano, (C$_1$–C$_4$)alkyl, (C$_1$–C$_4$)alkoxy, (C$_1$–C$_4$)alklthio, (C$_1$–C$_4$)alkylsulfinyl and (C$_1$–C$_4$)alkylsulfonyl; a (C$_2$ to C$_4$)alkynoxy group, an unsubstituted (C$_6$ to C$_{10}$)aryloxy group or (C$_6$ to C$_{10}$)aryloxy group substituted with up to three substituents selected from the group consisting of halogen, nitro, trihalomethyl, cyano, (C$_1$–C$_4$)alkyl, (C$_1$–C$_4$)alkoxy, (C$_1$–C$_4$)alklthio, (C$_1$–C$_4$)alkylsulfinyl and (C$_1$–C$_4$)alkylsulfonyl;or a hydroxy group; Q is an unsubstituted 1-(1,2,4-triazolyl) or 4-(1,2,4-triazolyl) or substituted 1-(1,2,4-triazolyl) or 4-(1,2,4-triazolyl-)with two substituents selected from the group consisting of halogen, (C$_1$–C$_4$)alkyl, nitro and cyano; X is hydrogen or CN;

m is in an integer with a value of zero or one; n is an integer with a value of one or two which comprises the reaction of an intermediate compound of the formula:

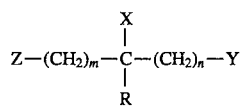

wherein Z, R, X, m and n are as defined above and Y is selected from halo, tosyl and mesyl with a triazole salt of the formula:

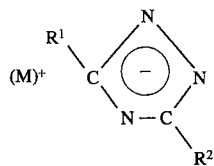

wherein M is a cation or a mixture of cations; $R^1$ and $R^2$ are the same or different and have the same definition as R; and the triazole salt is added to the intermediate compound in multiple additions;

such that the yield greater than about 94% are achieved.

15. The process of claim 14 wherein the triazole salt is added continuously.

16. The process of claim 14 wherein the triazole salt is sodium triazole and the intermediate compound is 2-chloromethyl-2-(4-chlorophenyl)hexane nitrile.

17. The process of claim 14 wherein the resulting triazole product is α-butyl-α-(4-chlorophenyl)-(1H-1,2,4-triazole)-1-propanenitrile.

18. The process of claim 14 wherein the triazole salt is sodium triazole and the intermediate compound is 1-chloro-2-cyano-2-phenyl-4-(4-chlorophenyl)butane.

19. The process of claim 14 wherein the resulting triazole product is α-[2-(4-chlorophenyl)] ethyl-α-phenyl-(1H-1,2,4-triazole)-1-propanenitrile.

* * * * *